(12) United States Patent
Spurr

(10) Patent No.: US 7,459,563 B2
(45) Date of Patent: Dec. 2, 2008

(54) PROCESS FOR THE PREPARATION OF ISONICOTINIC ACID DERIVATIVES

(75) Inventor: Paul Spurr, Riehen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 582 days.

(21) Appl. No.: 11/259,880

(22) Filed: Oct. 27, 2005

(65) Prior Publication Data

US 2006/0100440 A1    May 11, 2006

(30) Foreign Application Priority Data

Nov. 5, 2004   (EP)   .................................. 04105554

(51) Int. Cl.
*C07D 213/46*   (2006.01)
(52) U.S. Cl. ....................................................... 546/315
(58) Field of Classification Search ........................ None
See application file for complete search history.

(56) References Cited

U.S. PATENT DOCUMENTS

| | | | |
|---|---|---|---|
| 3,725,428 A | 4/1973 | Janiak |
| 4,028,374 A | 6/1977 | Pelose, Jr. et al. |
| 4,471,957 A | 9/1984 | Engalitcheff, Jr. |
| 5,099,021 A | 3/1992 | Worther et al. |
| 5,142,910 A | 9/1992 | Litchmann |
| 5,275,045 A | 1/1994 | Johnston et al. |
| 5,312,107 A | 5/1994 | Gvoich et al. |
| 5,348,519 A | 9/1994 | Prince et al. |
| 5,439,225 A | 8/1995 | Gvoich et al. |
| 6,521,754 B2 | 2/2003 | Alanine et al. |
| 6,548,495 B2 | 4/2003 | Adam et al. |
| 6,620,811 B2 | 9/2003 | Flohr et al. |
| 6,835,732 B2 | 12/2004 | Alanine et al. |
| 6,963,000 B2 | 11/2005 | Alanine et al. |
| 2003/0134854 A1 | 7/2003 | Flohr et al. |
| 2005/0026906 A1 | 2/2005 | Alanine et al. |
| 2006/0003986 A1 | 1/2006 | Alanine et al. |

FOREIGN PATENT DOCUMENTS

| | | |
|---|---|---|
| DE | 1953149 | 5/1970 |
| EP | 113219 | 7/1984 |
| EP | 0199400 | 10/1986 |
| EP | 295656 | 12/1988 |
| EP | 0295656 | 12/1988 |
| EP | 0343893 | 11/1989 |
| EP | 0404440 | 12/1990 |
| EP | 427963 | 5/1991 |
| EP | 0604657 | 7/1994 |
| FR | 2753970 | 4/1998 |
| GB | 1345552 | 1/1974 |
| GB | 1538822 | 1/1979 |
| WO | WO 99/24035 | 5/1999 |
| WO | WO 99/37630 | 7/1999 |
| WO | WO 00/18767 | 4/2000 |
| WO | WO 00/27819 | 5/2000 |
| WO | WO 01/10846 | 2/2001 |
| WO | WO 01/19360 | 3/2001 |
| WO | WO 01/29011 | 4/2001 |
| WO | WO 01/29012 | 4/2001 |
| WO | WO 01/97786 | 12/2001 |
| WO | WO 02/083665 | 10/2002 |
| WO | WO 03/043636 | 5/2003 |

OTHER PUBLICATIONS

Johnson et al., Journal of the Chemical Society, p. 796-880, (1970).
Bardhan, J., Journal of the Chemical Society, p. 2223-2232 (1929).
Locicero, et al., Journal of the American Chem. Society, vol. 74, pp. 2094-2097 (1952).
Colotta, et al., Arch. Pharm. Med. Chem. vol. 332, pp. 39-41 (1999).
Baraldi, et al., J. Med. Chem. vol. 39, pp. 1164-1171 (1996).
Li et al., J. Med. Chem. vol. 42, pp. 706-721 (1999).
Kim et al., J. Med. Chem. vol. 41, pp. 2835-2845 (1998).
Li et al., J. Med. Chem. vol. 41, pp. 3186-3201 (1998).
Baraldi, et al., J. Med. Chem. vol. 41, pp. 2126-2133 (1998).
Poulsen et al., Bioorganic & Medicinal Chem. vol. 6, pp. 619-641 (1998).
Müller et al., Bioorganic & Medicinal Chem., vol. 6, pp. 707-719 (1998).
Patent Abstracts of Japan, No. 10, (1999), JP11130761A.
Pandeya, et al., Indian Drugs, vol. 23(3), pp. 146-151 (1985).
Daidone et al., Il Farmaco vol. 44, No. 5, pp. 465-473 (1989).
The Merck Index, 12$^{th}$ Ed. P. 506, (1996).

(Continued)

*Primary Examiner*—Zinna N Davis
(74) *Attorney, Agent, or Firm*—George W. Johnston; Patricia S. Rocha-Tramaloni; Kimberly J. Prior

(57) ABSTRACT

The present invention relates to a process for the manufacture of compounds of formula Ia or Ib

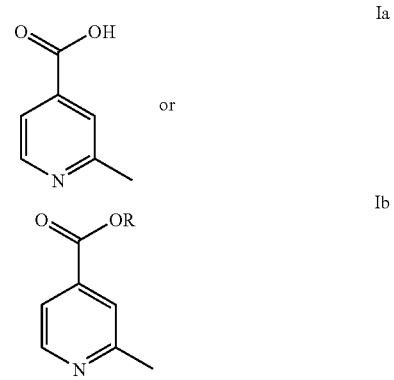

and pharmaceutically acceptable additional salts thereof, wherein R is lower alkyl. The compounds of formula Ia or Ib are valuable intermediate products for the manufacture of compounds that are pharmaceutically active as adenosine A2a receptor antagonist or metabotropic Glutamate receptor 2 antagonist. Such compounds are important in the regulation of many aspects of cellular metabolism and in the modulation of different central nervous system activities.

15 Claims, No Drawings

OTHER PUBLICATIONS

Bellamy et al., Tetrahedron Letters, vol. 25, No. 8, pp. 839-842 (1984).
Achmatowicz et al., Tetrahedron, vol. 27, pp. 1973-1996 (1971).
Boyer et al., J. Heterocyclic Chem. vol. 25, pp. 1003-1005 (1988).
Ohmori et al., J. Med. Chem. vol. 37, pp. 467-475 (1994).
Ishikawa et al., J. Med. Chem. vol. 28, pp. 1387-1393 (1985).
Fanta et al., Organic Synthesis, vol. 25, pp. 78-80 (1945).
Corey et al., J. Org. Chem. vol. 38, No. 18, p. 3224 (1973).
Eicher et al., Synthesis, pp. 755-762 (1996).
Widmer, Synthesis pp. 135-136 (1983).
Bowman et al., Org. Prep. Proc. Int. Briefs vol. 22, No. 5, pp. 636-638 (1990).
Quallich et al., Synthesis, pp. 51-53 (1993).
Auchampach et al., Am. J. Physiol., vol. 276, pp. H1113-H1116 (1999).
Haas et al., Naunyn Schmiedeberg's Arch. Pharmacol. vol. 362, pp. 375-381 (2000).
Dionisotti et al., Br. J. Pharmacol. vol. 121, pp. 353-360 (1997).
Abstract corresponding to FR 2753970 (B9), (1998).
Abstract corresponding to WO 00/27819 (B12), (2000).
Ragan, JA, et al., Synthesis, No. 4, pp. 483-486 (2002).

PROCESS FOR THE PREPARATION OF ISONICOTINIC ACID DERIVATIVES

BACKGROUND OF THE INVENTION

The compounds of formula Ia or Ib are valuable intermediate products for the manufacture of compounds which are pharmaceutically active as adenosine A2a receptor antagonist or metabotropic Glutamate receptor 2 antagonist. They are important in the regulation of many aspects of cellular metabolism and in the modulation of different central nervous system activities (WO 01/97786, WO 03/043636, and WO 02/083665).

SUMMARY OF THE INVENTION

The present invention provides a new process for preparing isonicotinic acid derivatives of formula Ia or Ib

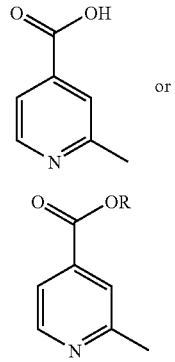

and pharmaceutically acceptable additional salts thereof, wherein R is lower alkyl.

The process is shown in Scheme 1:

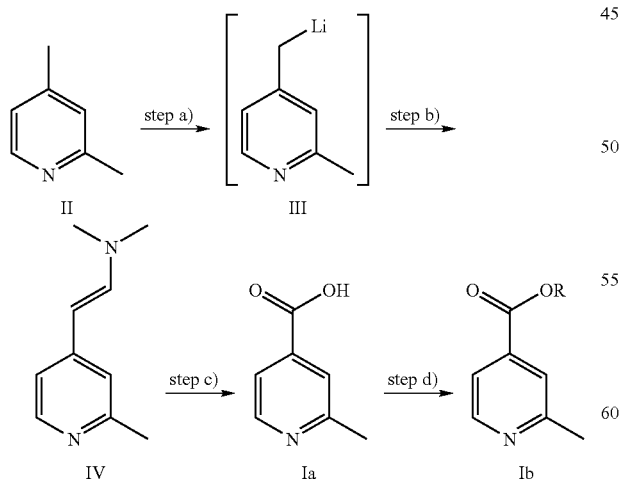

The new process is simple, cheap and efficient when compared with the process known in the art (R. Johnson, T. Lovet and T. Stevens, Journal of the Chemical Society 796, 1970; J. Bardhan, Journal of the Chemical Society 2223, 1929; J. LoCicero and R. Johnson, Journal of the American Chemical Society, 74, 2094-7; 1952).

DETAILED DESCRIPTION OF THE INVENTION

The process of the invention comprises the step of a) lithiating a compound of formula II, which is commercially available,

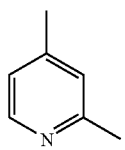

with lithium diethylamide to produce a lithiated compound of formula III;

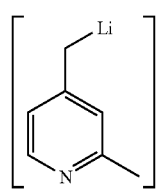

b) reacting the compound of formula III with dimethylformamide (DMF) to produce the compound of formula IV;

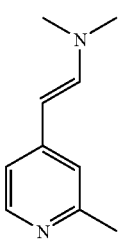

c) oxidizing the compound of formula IV with $O_3$ and $H_2O_2$ to produce compound of formula Ia;

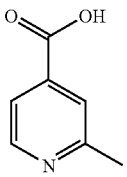

d) if desired, esterifying the compound of formula Ia with an alcohol of the formula ROH, which is commercially available, to produce compound of formula Ib;

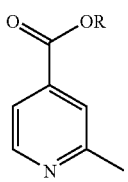

wherein R is as defined above.

The term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1-4 carbon atoms. A more preferred lower alkyl group is methyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

Step a)

Step a) comprises lithiating 2,4-dimethyl-pyridine of formula II with a lithiating agent, such as lithium diethylamide to a lithiated compound of formula III.

Typically, the reaction is performed in an organic solvent, such as ether, hydrocarbon or tetrahydrofuran (THF), preferably THF.

The reaction temperature is typically in the range of −70° C. to 0° C., preferably between −70° C. to −50° C.

The reaction time generally is 0.5 to 3 hours, preferably 1 hour.

Step b)

Step b) comprises reacting a compound of formula III with DMF to produce the compound of formula IV Typically the reaction is performed in an organic solution of the compound of formula III to which DMF is added.

The reaction temperature is typically in the range of −70 to 0° C., preferably −60° C. to −40° C.

The reaction generally is 0.5 to 3 hours, preferably 1 hour.

The general principle of reaction steps a) and b) are described in J. Ragan, B. Jones, C. Meltz and J. Teixeira, Synthesis, 483 (4) 2002.

Step c)

Step c) comprises oxidizing the compound of formula IV with $O_3$ and $H_2O_2$ to produce compound of formula Ia.

The reaction of step c) is typically performed in an organic solvent, such as an organic acid, an alcohol, a chlorinated hydrocarbon or an ester, containing small amounts of water, such as 1-10%, preferably acetic acid containing 5% of water. The inclusion of water avoids the build-up of dangerous peroxides in the reaction mixture, especially in the presence of a protic solvent. The ozonolysis is performed at the temperature range of 0° C. to 50° C., preferably 15° C. to 20° C. for typically 0.5-3 hours, preferably 1 hour.

The reaction mixture is further oxidized with $H_2O_2$, typically for a time range of 0.5-3 hours. In the absence of an additional acid, the oxidation with $H_2O_2$ requires heating to a temperature range of 30 to 100° C., preferably 50° C.

In the presence of an additional acid, such as hydrochloric acid, nitric acid, sulfuric acid, phosphoric acid, citric acid, formic acid, methanesulfonic acid, p-toluenesulfonic acid, preferably hydrochloric acid, sulfuric acid or formic acid, the subsequent oxidation with $H_2O_2$ may be achieved at ambient temperature. $H_2O_2$ may be added from the start or after the ozonolysis reaction. Optionally, the added water is substituted by aqueous $H_2O_2$, (preferably ca. 1 equ. constituting also ~5% water content) which provides both the water and the additional oxidant for the second stage from the outset.

Step d)

Step d) comprises esterifying a compound of formula Ia with an alcohol of formula ROH to produce compound of formula Ib.

Esterifying with an alcohol of formula ROH to produce compound of formula Ib is typically performed in an alcohol, such as methanol, ethanol, n-propanol, i-propanol, n-butanol, i-butanol, 2-butanol or t-butanol, preferably methanol in the presence of a mineral acid or a substance generating a mineral acid in situ, e.g. $SOCl_2$.

The reaction temperature depends on the boiling temperature of the alcohol used and, as a rule, lies in the range of 60° C. to 150° C.

The reaction time is about 1 to 24 hours, preferably 1 hour.

The following examples shall illustrate the invention in more detail without limiting it.

EXAMPLE 1

Preparation of dimethyl-[2-(2-methyl-pyridin-4-yl)-vinyl]-amine

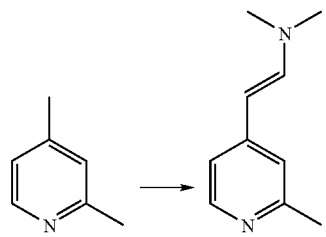

11.05 g 2,4-Lutidine (0.1 mol) were dissolved in 50 ml THF. The solution was cooled and stirred, maintaining the temperature at between −70 to −50° C. 81.25 ml nBuLi (0.13 mol) was added over 0.25 hour. The dark red solution was stirred for a further 0.5 hour, then 15.14 ml diethylamine (0.145 mol) was added in one portion producing an orange suspension. After a 0.5 hour, 15.5 ml DMF (0.2 mol) was added. The brown-red solution was stirred for 1 hour then quenched with 50 ml 50% saturated aqueous ammonium chloride solution. Upon warming to ambient temperature, the reaction mixture was extracted with tert. butyl methyl ether (TBME) (3×100 ml), and the combined organic phases were washed with 50 ml $H_2O$, dried over $Na_2SO_4$, filtered and concentrated under reduced pressure (45° C./450-20 mbar) providing an orange-red oil (14.8 g, 91%) which was sufficiently pure (Gas Liquid Chromatography (GLC) 98 area %) to be used directly in the next step.

EXAMPLE 2 i) Preparation of 2-methyl-isonicotinic acid (no additional acid, 50° C.)

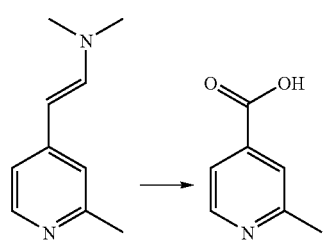

1.63 g Dimethyl-[2-(2-methyl-pyridin-4-yl)-vinyl]-amine (10 mmol) were dissolved in 19 ml acetic acid containing 1 ml H$_2$O. To the red solution maintained and stirred at ca. 15-20° C. was passed O$_3$ (~85 mmol/hour) for 1 hour. The reaction was mildly exothermic, changing in appearance from an orange (10 min) to a yellow solution (15 min) then from a yellow (20 min) to a white suspension (30 min). Excess ozone was purged with argon until a peroxide test was essentially negative. 1.02 ml 30% aqueous H$_2$O$_2$ (10 mmol) was added in one portion, and the resulting yellow suspension was stirred at 50° C. for 2 hours during which time a white suspension was formed. With the aid of toluene, the aqueous acetic acid solvent was removed under reduced pressure (45° C./100-50 mbar). The white residue was briefly digested in 25 ml tert. butyl methyl ether (TBME) at 40° C. then at ambient temperature for 30 min. The product was filtered, washed with TBME and dried for 2 hours at 45° C./25 mbar: 1.17 g (85%) biege crystals (GLC 98 area %, as trimethylsilylester).

$^1$H-NMR: (400 MHz, D$_6$ DMSO): δ=2.54 (s, 3H), 7.59 (dd, 1H), 7.70 (s, 1H), 8.60 (dd, 1H)

ii) Preparation of 2-methyl-isonicotinic acid (additional acid, ambient temperature)

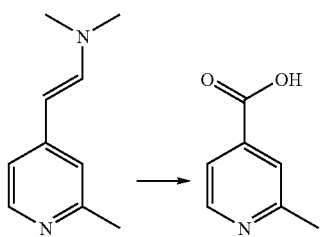

The reaction procedure was performed according to i). After purging with argon, 1.16 ml 98% aqueous formic acid (30 mmol) and 1.02 ml 30% aqueous H$_2$O$_2$ (10 mmol) were added in one portion, and the suspension was stirred at ambient temperature for 3 hours. The solvent was removed with the aid of toluene under reduced pressure (45° C./80-20 mbar). The residue was briefly digested in 25 ml tert. butyl methyl ether (TBME) at 40° C. then at ambient temperature for 30 min. The product was filtered, washed with TBME and dried for 2 hours at 45° C./25 mbar: 1.17 g pale orange crystals (GLC 99 area %, as trimethylsilylester).

iii) Preparation of 2-Methyl-isonicotinic acid.H$_2$SO$_4$

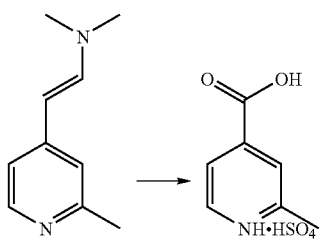

The ozonolysis procedure was performed as according to i) in the presence of 1 eq. 30% aqueous H$_2$O$_2$ on a 2 mmol scale. After purging with argon, 0.12 ml concentrated H$_2$SO$_4$ (2.1 mmol) was added in one portion, and the yellow suspension was stirred at ambient temperature for 1 hour. The solvent was removed with the aid of toluene under reduced pressure (45° C./80-20 mbar). The residue was briefly digested in 5 ml THF at 50° C. then at ambient temperature for 30 min. The product was filtered, washed with THF and dried for 1 hour at 45° C./20 mbar: 0.43 g (92%) pale yellow crystals (HPLC 82 area %).

iv) Preparation of 2-methyl-isonicotinic acid.HCl

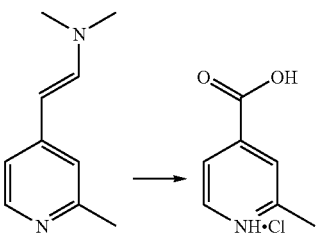

The reaction procedure was performed as according to iii) on a 2 mmol scale. After purging with argon, 1.1 ml 37% aqueous HCl (2 eq.) was added in one portion, and the suspension was stirred at ambient temperature for 1 hour. The solvent was removed with the aid of toluene under reduced pressure (45° C./80-20 mbar). The residue was briefly digested in 5 ml THF at 50° C. then at ambient temperature for 30 min. The product was filtered, washed with THF and dried for 1 hour at 45° C./20 mbar: 0.33 g (94%) pink crystals (HPLC 88 area %, GLC 98 area % as trimethylsilylester).

$^1$H-NMR: (400 MHz, D$_6$ DMSO): δ=2.77 (s, 3H), 8.03 (dd, 1H), 8017 (s, 1H), 8.83 (dd, 1H)

EXAMPLE 3

Preparation of methyl 2-methyl-isonicotinate

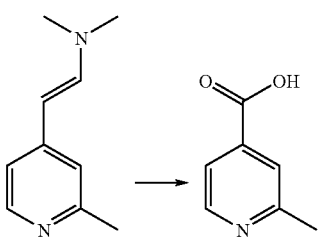

The reaction procedure was performed as according to Example 2 iv) on a 10 mmol scale but with the addition of 37% aqueous HCl (2 eq.) and 30% aqueous H$_2$O$_2$ (1 eq.) after the initial ozonolysis step. The crude product was taken in 10 ml MeOH, the suspension cooled to ca. 5° C. and 1.62 ml thionyl chloride (SOCl$_2$) (22 mmol) were added cautiously. The reaction mixture was heated at 65° C. for 1 hour during which a yellow suspension transformed into an orange solution. The solvent was removed under reduced pressure (45° C./200-20 mbar), and the residue was distributed between 20 ml ethyl acetate (EtOAc) and 20 ml saturated aqueous NaHCO$_3$. The aqueous phase was separated and extracted with EtOAc (2×20 ml). The combined organic phases were washed with 20 ml saturated aqueous NaHCO$_3$, dried over Na$_2$SO$_4$, filtered and concentrated under reduced pressure (45° C./150-20 mbar) providing an orange-red oil (1.19 g, 79%, GLC 100 area %).

$^1$H-NMR: (400 MHz, CDCl$_3$): δ=2.63 (s, 3H), 3.95 (s, 3H), 7.63 (dd, 1H), 7.71 (s, 1H), 8.65 (dd, 1H) MS: 151.0 (M$^+$)

The invention claimed is:

1. A process for the manufacture of a compound of formula Ia or Ib

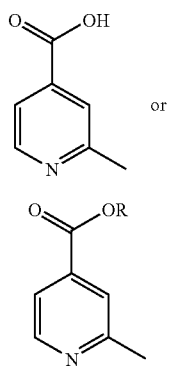

or a pharmaceutically acceptable additional salt thereof, wherein R is lower alkyl; comprising a) lithiating a compound of formula II

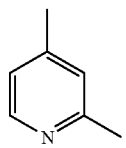

with a lithiating agent to produce a lithiated compound of formula III

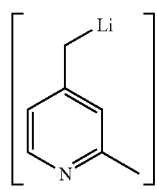

b) reacting of the compound of formula III with DMF to produce the compound of formula IV

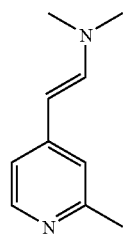

c) oxidizing the compound of formula IV with O$_3$ and H$_2$O$_2$ to produce compound of formula Ia;

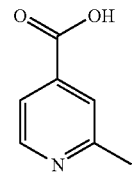

d) optionally, esterifying a compound of formula Ia with an alcohol of formula ROH to produce compound of formula Ib;

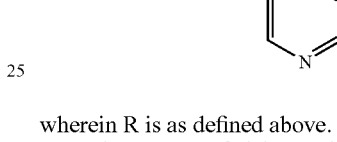

wherein R is as defined above.

2. The process of claim 1 wherein R is methyl.

3. The process of claim 1 wherein the lithiating agent is lithium diethylamide.

4. The process of claim 1 wherein step a) is performed in an organic solvent at a temperature of −70° C. to 0° C.

5. The process of claim 4 wherein the organic solvent is THF, and the temperature is −70° C. to −50° C.

6. The process of claim 1 wherein step b) comprises reacting compound of formula II with DMF at a temperature of −70° C. to 0° C.

7. The process of claim 6 wherein the temperature is −60° C. to −40° C.

8. The process of claim 1 wherein the ozonolysis of step c) is performed in an organic solvent containing 1-10% water at a temperature of 0° C. to 50° C.

9. The process of claim 8 wherein the organic solvent is acetic acid, the water content is 5% and the temperature is 15° C. to 20° C.

10. The process of claim 1 wherein the oxidation with H$_2$O$_2$ of step c) is performed in the absence of an additional acid at a temperature of 30° C. to 100° C.

11. The process of claim 10 wherein the temperature is 40° C. to 60° C.

12. The process of claim 1 wherein the oxidation with H$_2$O$_2$ in step c) is performed in the presence of an additional acid at ambient temperature.

13. The process of claim 12 wherein the additional acid is hydrochloric acid, sulfuric acid or formic acid.

14. The process of claim 1 wherein step d) is performed in an alcohol in the presence of a mineral acid or a substance generating a mineral acid at a temperature of 60° C. to 150° C.

15. The process of claim 14 wherein the alcohol is methanol, the substance generating a mineral acid is SOCl$_2$ and the temperature is 60° C. to 70° C.

* * * * *